(12) United States Patent
Thomas

(10) Patent No.: US 7,455,812 B2
(45) Date of Patent: Nov. 25, 2008

(54) METHOD AND APPARATUS FOR CONTROLLED REOXYGENATION

(75) Inventor: Neil J. Thomas, Chicago, IL (US)

(73) Assignee: Rheoxtech, LLC, Chicago, IL (US)

( * ) Notice: Subject to any disclaimer, the term of this patent is extended or adjusted under 35 U.S.C. 154(b) by 290 days.

(21) Appl. No.: 10/869,739

(22) Filed: Jun. 16, 2004

(65) Prior Publication Data

US 2005/0084416 A1    Apr. 21, 2005

Related U.S. Application Data

(60) Provisional application No. 60/511,837, filed on Oct. 16, 2003.

(51) Int. Cl.
  *A61M 1/00* (2006.01)
  *A61M 37/00* (2006.01)
  *B01D 11/00* (2006.01)

(52) U.S. Cl. ............... 422/45; 604/4.01; 604/6.13; 604/6.14; 422/44; 422/46; 422/47; 422/48; 210/644

(58) Field of Classification Search ............ 604/65–67, 604/4.01–6.16, 8–10, 19, 27, 29, 113, 114, 604/259; 422/44–48; 210/644, 634, 646, 210/647; 600/16–18, 322, 323
See application file for complete search history.

(56) References Cited

U.S. PATENT DOCUMENTS

| 4,466,804 | A | * | 8/1984 | Hino ..................... 604/6.14 |
| 4,540,399 | A |   | 9/1985 | Litzie et al. ................ 607/4 |
| 5,011,469 | A | * | 4/1991 | Buckberg et al. ......... 604/6.11 |
| 5,322,500 | A |   | 6/1994 | Johnson et al. |
| 5,391,142 | A | * | 2/1995 | Sites et al. ................ 604/6.13 |
| 5,725,492 | A | * | 3/1998 | Igo et al. ................. 604/6.11 |
| 5,770,073 | A |   | 6/1998 | Bach et al. |
| 5,935,093 | A |   | 8/1999 | Elgas et al. |
| 6,039,078 | A | * | 3/2000 | Tamari ..................... 138/30 |
| 6,071,258 | A | * | 6/2000 | Dalke et al. ............... 604/5.01 |
| 6,248,087 | B1 | * | 6/2001 | Spears et al. .............. 604/6.14 |
| 6,387,323 | B1 | * | 5/2002 | Afzal et al. ................ 422/45 |

(Continued)

FOREIGN PATENT DOCUMENTS

FR    2 513 884 A    4/1983

(Continued)

OTHER PUBLICATIONS

Neil J. Thomas et al., "Controlled Cardiac Reoxygenation in Adults with Ischemic Heart Disease," Journal of Thoracic and Cardiovascular Surgery, Mar. 1999, pp. 630-632.*

(Continued)

*Primary Examiner*—T. Zalukaeva
*Assistant Examiner*—Phil Wiest
(74) *Attorney, Agent, or Firm*—King & Spalding

(57) ABSTRACT

A method and apparatus for performing coronary perfusion and cardiac reoxygenation that enables accurate control of oxygen levels in blood used for the coronary circulation. Deoxygenated blood and oxygenated blood are collected and oxygen levels are measured by sensors. The deoxygenated and oxygenated blood is then mixed and the mixed blood is measured by another sensor. The sensors provide data used to provide real-time oxygen level measurement and adjustment for blood supplied for coronary circulation.

13 Claims, 5 Drawing Sheets

U.S. PATENT DOCUMENTS

| | | | |
|---|---|---|---|
| 6,443,609 B2* | 9/2002 | Short | 366/152.1 |
| 6,454,999 B1 | 9/2002 | Farhangnia et al. | |
| 6,607,698 B1* | 8/2003 | Spears et al. | 422/45 |
| 6,613,008 B2* | 9/2003 | Aboul-Hosn et al. | 604/5.01 |
| 6,730,267 B2* | 5/2004 | Stringer et al. | 422/45 |
| 6,746,417 B2* | 6/2004 | Spears et al. | 604/6.14 |
| 6,918,887 B1* | 7/2005 | Gremel et al. | 604/6.09 |
| 6,974,435 B2* | 12/2005 | Daw et al. | 604/6.14 |
| 7,022,099 B2* | 4/2006 | Litzie et al. | 604/6.09 |
| 2002/0085952 A1 | 7/2002 | Ellingboe et al. | |
| 2005/0063860 A1 | 3/2005 | Carpenter et al. | |

FOREIGN PATENT DOCUMENTS

| | | |
|---|---|---|
| FR | 0 357 338 A2 | 3/1990 |
| FR | 2 648 714 | 12/1990 |
| WO | WO 99/08733 | 2/1999 |
| WO | WO 99/08734 A1 | 2/1999 |
| WO | WO 00/16825 A1 | 3/2000 |
| WO | WO 00/47266 A1 | 8/2000 |
| WO | WO 03/070300 A1 | 8/2003 |

OTHER PUBLICATIONS

"Controlled Cardiac Reoxygenation in Adults with Ischemic Heart Disease," The Journal of Thoracic and Cardiovascular Surgery, Mar. 1999.

"CDI Systems 500 GUI," http://www.idsa.org/whatis/seewhat/idea99/winners/cdi500gui.htm.

"Normoxic Cardiopulmonary Bypass Reduces Oxidative Myocardial Damage and Nitric Oxide During Cardiac Operations in the Adult," Ihnken et al., Cardiovascular Surgery, vol. 116, No. 2, 1998.

"Delayed Cardioplegic Reoxygenation Reduces Reoxygenation Injury in Cyanotic Immature Hearts," Ihnken et al., The Society of Thoracic Surgeons, 1998.

"Detrimental Effects of Cardiopulmonary Bypass in Cyanotic Infants: Preventing the Reoxygenation Injury," Allen et al., The Society of Thoracic Surgeons, 1997.

"3M Wins Medical Design Excellence Award for Blood Parameter Monitoring Device," http://3m.com/profile/pressbox/cdiaward.html.

"Cardioplegia Volume Tracking Feature Adds Convenience, Value to 3M Sarns System 8000," http://3m.com/profile/pressbox/cardiop.html.

Supplementary Partial European Search Report dated Feb. 20, 2007.

* cited by examiner

METHOD AND APPARATUS FOR CONTROLLED REOXYGENATION

RELATED APPLICATIONS

This application claims the benefit of U.S. Provisional Application Ser. No. 60/511,837 filed Oct. 16, 2003, the entirety of which is incorporated by reference.

GENERAL

The present invention relates to medical devices for use in heart surgery. In particular, the present invention pertains to a method and apparatus for controlled coronary perfusion and/or cardiac reoxygenation.

During a heart operation, the functions of a patient's heart and lungs are often bypassed through cardiopulmonary bypass (CPB) equipment, also known as a heart-lung machine. The heart-lung machine's main circuit, in essence, consists of a pump (to replace the functions of the heart) and an oxygenator (to replace the function of the lungs). When connected to the patient by way of large insertion tubes known as cannulae, the heart-lung machine completes a continuous tubing circuit in which carbon dioxide is removed from the patient's blood, oxygen is added, and the reoxygenated blood is pumped back into the patient's body, usually through the aorta or one of its major braches.

The heart-lung machine drains deoxygenated, venous (blue) blood from the right atrium of the patient's heart or from one or both vena cavae into a reservoir. From the reservoir, the deoxygenated blood is pumped through an oxygenator. The oxygenator, usually by way of a multiple hollow-fiber membrane, exposes the blood to gaseous oxygen. Due to dissolution and a direct biochemical reaction between hemoglobin and oxygen molecules, the blood becomes oxygenated. The oxygenated blood (red blood) is then pumped back into the body through an artery, typically, the aorta or one of its major branches.

The heart-lung machine also routinely perform the tasks of salvaging shed blood that leaves the circulation through the surgical wound or open cardiac chambers, cooling or heating of the blood and, therefore, the patient, or introduction of medications directly into the blood stream. Gaseous anesthetic agents or room air may also be introduced via the oxygenator.

During cardiopulmonary bypass (CPB), cardioplegia is typically used to protect and, in some situations, resuscitate the heart. Cardioplegia is typically a combination of blood and saline (crystalloid) solution with various components used to stop the heart's electrical and, ultimately, its mechanical activity. The cardioplegia circuit comprises tubing, a separate pump or pump head, and a mixing system that controls the ratio of crystalloid to blood delivered to the heart (typically 1:3 or 1:4). A standard cardioplegia circuit allows for either streaming oxygenated blood from the oxygenator to mix with a crystalloid solution in a pre-specified ratio or for the pooling of blood in a reservoir; therefore allowing dilution with the crystalloid within the reservoir in a given ratio. The oxygenated blood and crystalloid cardioplegia mixture, typically known as a "perfusate" or a "reperfusate" is then applied to the heart. The reperfusate, or cardioplegic solution, includes varying concentrations of potassium chloride that arrests the heart. Because the reperfusate also applies oxygenated blood to the heart tissues via the coronary circulation, the arrested heart continues to receive oxygen during the arrest phase or cardioplegia phase of a cardiac operation. This ongoing oxygen delivery to the arrested heart typically occurs at least intermittently; however with some perfusion strategies, it may occur continuously or almost continuously.

For myocardial protection, a surgeon separates the blood supply sent to the aorta (or another major branch) for total body perfusion and the blood supply sent to the coronary circulation (via the aortic root, the coronary sinus or previously constructed bypass grafts). In so doing, the heart surgeon limits the amount of oxygen to which the heart is exposed and can precisely control other components of the coronary perfusate by designing a cardioplegia solution that contains protective nutrients for cardiac resuscitation and protection when the heart is cut off from the perfusion of the rest of the body. Circulation to the remainder of the patient's body is controlled by the perfusionist and the anesthesiologist working in concert to ensure, in particular, the required amount of oxygenation that must be provided to the patient's brain, kidneys, liver and other major organ systems. Accordingly, significantly high levels of oxygen are present in the blood used for total body perfusion. In typical CPB equipment, including the cardioplegia circuit, the coronary circulation is exposed to the same levels of oxygen.

The standard cardioplegia circuit approach, however, may lead to reperfusion injury especially for patients in whom ongoing or antecedent myocardial tissue ischemia (an unfavorable imbalance between the demand of oxygen and the supply of oxygen) is present prior to commencing the surgical procedure or prior to commencing CPB and cardioplegic arrest. Variable degrees of surgically induced ischemia may also develop, while the heart is arrested during surgery and receiving oxygen intermittently, that can predispose to reperfusion injury as well. To illustrate this point, it has been shown, experimentally and in clinical situations, that uncontrolled or abrupt oxygen re-exposure is injurious in a number of situations in which hypoxic cardiac (myocardial/conduction/endothelial) tissue is present. Examples might include children with complex congenital heart lesions leading to cyanosis or adult patients with unstable coronary syndromes that have been clinically protracted.

Reperfusion injury comprises a number of different and important cellular and molecular processes that amplify or aggravate an ischemic insult. During a period of a variable degree of ischemia (when blood flow and, therefore, oxygen delivery to one or more areas of the heart is limited), the affected cells undergo alterations from aerobic to anaerobic metabolism. As the intensity and/or duration of the ischemia increase, the affected tissues can become overwhelmed by reperfusion and the reintroduction of oxygen when and if it occurs. The paradox lies in the realization that while the restoration of the availability of oxygen (and blood flow) is ultimately necessary to restore tissue integrity and insure survival, under certain conditions, this can also be detrimental. If reperfusion can be established after only brief or relatively mild conditions of ischemia, the tendency toward cell injury is reduced and natural restorative processes can and do reverse the ischemic injury.

Increasing degrees of reversible ion (sodium, potassium, calcium) dys-homeostasis or imbalance across the cell and mitochondrial membranes begin to develop during the early stages of an ischemic insult and worsen or progress with time and with increasing intensity of the ischemia. In other words, as ischemic conditions progress, the cells develop ion shifts that lead to increasingly unfavorable conditions. If flow and oxygen delivery are suddenly reestablished, the affected tissue/cells can be overwhelmed by unfavorable ion flux (most importantly, calcium influx), pressure alterations and pH changes that ultimately lead to explosive cell injury and death by several different mechanisms. The re-exposure of the milieu to molecular oxygen and the resultant re-energization of the cell lead to contraction necrosis due to calcium overload in the worst-case scenario. Less severe forms of calcium overload can lead to rigor contracture also leading to incremental cellular dysfunction and injury.

Cyanotic conditions imply normal flow of deoxygenated blood, and ischemic conditions imply lack of flow of normally oxygenated blood. At the tissue level, however, overwhelming oxidative stress has been shown to be dangerous in both settings, albeit by somewhat different mechanisms. Significant degrees of oxidative stress lead to the formation of highly reactive and injurious molecules that are formed by the addition of oxygen into an unfavorable milieu. An example of this would be the formation of peroxynitrite after reoxygenation of cyanotic tissues, which may adapt to such conditions by producing increasing levels of nitric oxide (caused by the increased activity of endothelial cell derived inducible nitric oxide synthetase [iNOS]). The presence of such molecules after reoxygenation leads to cellular injury through a process known as lipid peroxidation in which the cell membrane lipid bilayer is attacked and rendered permeable or worse. Such cell membrane damage can lead to cellular destruction, which is additive after a previous ischemic insult and which has been shown to be very poorly tolerated after cyanosis. This is particularly true in cyanotic children who are abruptly reoxygenated on CPB during surgery to correct often complex congenital heart lesions.

Finally, we are becoming aware of a number of other mechanisms by which reperfusion injury can aggravate cellular or tissue injury following ischemia. Such transcriptionally related events add an increment of cellular death and tissue dysfunction much later (days to weeks) after the initial insult. These events relate to the activation of the inflammatory pathways, the release of cytokines, upregulation of intracellular transcription factors (like nuclear factor Kappa B). Each contributes to adhesion of leukocytes and the resultant inflammatory injury and programmed cell death (apoptosis) can also be activated by the transcription of several apoptosis genes that have been identified.

Recent preliminary research data suggests that all of the processes discussed above can be favorably altered by controlled reoxygenation. Plausible hypotheses have been offered for favorably manipulating these processes. The clinical work has shown promise that the concept of controlled reoxygenation in adult cardiac surgery improves the protection of the previously ischemic heart from injury. The reperfusion of the adult human heart with venous blood cardioplegia in a clinical setting has been described and also shown a survival benefit in an animal experiment designed to exploit the fatal nature of overwhelming reperfusion injury under certain circumstances. This demonstrates that a reduction in oxidative stress at the time of controlled reperfusion after particularly severe ischemia is, indeed, protective. This may work by lowering the gradient of oxygen delivery during initial reperfusion to the previously hypoxic areas allowing time for improved ion homeostasis (prior to re-exposure to molecular oxygen), and reducing the tendency for the cells to experience calcium overload resulting in contraction necrosis (one form of reperfusion injury). A brief period of deoxygenated blood/cardioplegic reperfusion followed by a gradual increase of re perfusate $pO_2$ can also reduce lipid peroxidation of cellular membranes; another immediate form of reperfusion injury.

In order to control cardiac reoxygenation, perfusionists (technicians that operate the heart-lung machine) have spliced a line of tubing into the cardioplegia circuit of a heart-lung machine that allows venous blood to be pumped through the cardioplegia circuit to the heart to exploit this enhanced protection. Oxygen levels have been lowered to more physiologic ranges. In the case of ischemic myocardial tissue, this means exposure of the heart to $pO_2$'s in the venous range, gradually raising the $pO_2$ by mixing arterial and venous blood and by eventually allowing only arterial blood to the heart. In addition, the percentage of oxygen exposed directly to the membrane oxygenator has been reduced. By adding a tank of room air to the circuit, an air-oxygen mixture is achieved such that the resultant blood $pO_2$ is more acceptable and more physiologic at all points while CPB is used in any given patient (cyanotic child, adult with coronary heart disease or any other situation).

While real time read-outs of blood or cardioplegia circuit $pO_2$ are available, the $pO_2$ of sanguineous cardioplegia is typically not considered. Further, the splicing arrangement that I have pioneered is limited in its ability to precisely control and adjust the the $pO_2$ of blood cardioplegia. Accordingly, abrupt changes from deoxygenated blood to oxygenated blood are possible under the splicing arrangement. As such, difficulties exist in providing controlled reoxygenation due to a lack of precision in the adjustment and real-time measurement of oxygen levels in the blood provided to the coronary circulation.

BRIEF SUMMARY

The presently preferred embodiments are directed toward a stand-alone device or component of another device or system that controls oxygenation levels of blood presented for reintroduction to the human body and, in particular, the human heart. As noted above, for a number of reasons it may be desirable to control oxygen levels for coronary reperfusion after ischemia in an effort to control cardiac reoxygenation and to mitigate additive injury that occurs under certain conditions.

By utilizing the tube splicing technique described above and with the aorta and the coronary circulations separated by a clamp, separate oxygenation levels have been achieved and thus provided to the body through the aorta (or other major branch) and to the heart. The surgeon can, under these circumstances, but to only a certain degree, control cardiac reoxygenation. The method is problematic, however, because it does not provide for an accurate way to precisely control the oxygenation levels of blood in real-time. The surgeon and the perfusionist working together guess at the actual levels of blood $pO_2$. Further, while blood gas determinations can be obtained during such controlled reperfusion attempts, the data is delayed and real-time adjustments are, at best, difficult and approximate.

The presently preferred embodiments improve upon the splicing techniques. A presently preferred embodiment utilizes blood from the venous reservoir and from an oxygenator and allows for precise mixing and a real-time read out of blood $pO_2$ levels. Cardiopulmonary bypass tubing from the venous reservoir and arterial (post-oxygenator) lines feed the system to allow mixing of desaturated and arterialized blood from the bypass circuit. In a presently preferred embodiment, sensors measure the oxygen saturation and $pO_2$ levels of incoming blood received from the oxgenator, venous blood received from the patient, and outgoing mixed blood used for coronary perfusion.

In one embodiment, a microprocessor (or a combination of microprocessors) receives the data from the sensors and provides feedback to the surgeon and/or perfusionist. In another embodiment, this data is used by the microprocessor to control the pump heads within the system, providing adjustments to the venous and arterial mixture.

Oxygenators may not necessarily provide entirely consistent results in oxygen saturation or $pO_2$, and, in particular, may provide different results on a patient-by-patient basis and from time to time within the same patient. The presently preferred embodiments seek to provide a substantially constant level of oxygen that is sent through the system for coronary perfusion that is also continuously adjustable. These adjustments may be set by the perfusionist and controlled within the system through the microprocessors management of data collected by the sensors. Thus, despite potential variation in the oxygen levels, e.g. partial pressures, of the oxygenated blood exiting the oxygenator and in the venous reservoir, the blood pumped to the coronary circulation may be accurately regulated.

The microprocessor may receive further direction to adjust (up or down) the $pO_2$ of the output blood. This direction may be controlled and/or programmed by a dial, digital read-out, or touch screen of desired levels of oxygen within the admixture of blood from the venous and arterial sides of the pump that the surgeon or perfusionist may select for any given situation. In this regard, the microprocessor may control the internal pump heads, reservoir, and/or internal bladders to provide a real-time adjustment of the oxygen level in the blood pumped to the coronary circulation.

In a first aspect, a perfusion control input receives a desired blood oxygen level, a venous blood sensor measures oxygen levels in venous blood, an oxygenated blood sensor measures oxygen levels in oxygenated blood, a mixed blood supply receives venous blood and oxygenated blood, and a mixed blood sensor measures oxygen levels in the mixed blood supply. Venous and oxygenated blood pumps are provided to move venous and oxygenated blood, respectively. A microprocessor receives data from the perfusion control input and the sensors and instructs the pumps to increase, decrease, or completely stop, blood flow to reach the desired blood oxygen level.

In a second aspect, a venous drainage pathway, a systemic perfusion pathway, and cardioplegia delivery pathway are provided. An oxygenator is connected with the venous drainage pathway and has one or more outputs connected with the systemic delivery pathway and an oxygenation controller. The oxygenation controller reads data from at least one blood oxygen level sensor and mixes blood from the venous drainage pathway and systemic delivery pathway to create a mixed blood supply.

In a third aspect, a venous blood supply, an oxygenated blood supply, at least one sensor for measuring blood oxygen levels, and a desired outputted blood oxygen level are provided. Blood from the venous blood supply is mixed with blood from the oxgyenated blood supply. Blood oxygen level data is collected. The mixed blood oxygen level is then compared with the desired blood oxygen level and the mixture of blood is adjusted in response to the comparison.

In a fourth aspect, a microprocessor is provided with one or more memories operable to store data corresponding to a real-time blood oxygen level for deoxygenated blood, data corresponding to a real-time blood oxygen level for oxygenated blood, data corresponding to a real-time blood oxygen level corresponding to a mixture of deoxygenated and oxygenated blood, and data corresponding to a desired blood oxygen level for the mixture of deoxygenated and oxygenated blood. The microprocessor controls the amount of deoxygenated and oxygenated blood provided to the mixture of deoxygenated and oxygenated blood.

In a fifth aspect, deoxygenated and oxygenated blood supplies are provided. The deoxygenated blood supply may be venous blood or another source of blood with oxygen levels that are lower than the oxygenated blood supply. The oxygenated blood supply may be blood that has passed through an oxygenator or another source of blood with oxygen levels that are higher than the deoxygenated blood. The oxygen levels may be, for example, partial pressure of oxygen or oxygen saturation. Real-time blood oxygen level and flow rate data for the deoxygenated blood and real-time blood oxygen level and flow rate data for the oxygenated blood is received. Blood from the dexogyenated blood supply is mixed with blood from the oxygenated blood supply. Real-time blood oxygen level data for the mixed blood is received and flow rates of the oxygenated blood and/or deoxygenated blood are adjusted.

In a sixth aspect, a perfusion control input, a venous blood supply input, an oxygenated blood supply input, and a mixed blood line connected with the venous blood supply and oxygenated blood supply inputs are provided. A mixed blood sensor measures blood oxygen levels in the mixed blood line and a microprocessor receives data from the perfusion control input and mixed blood sensor and controls the mixture of the venous blood with the oxygenated blood.

In a seventh aspect, reservoirs are provided to hold deoxygenated blood, oxygenated blood, and a mixture of deoxygenated and oxygenated blood for coronary circulation. Sensors are provided to measure oxygen levels in each of the reservoirs.

In an eighth aspect, blood lines are provided to hold deoxygenated blood, oxygenated blood, and a mixture of deoxygenated and oxygenated blood for coronary circulation. Sensors are provided to measure oxygen levels in each of the blood lines.

In a ninth aspect, blood supplies are provided to hold deoxygenated blood, oxygenated blood, and a mixture of deoxygenated and oxygenated blood for coronary circulation. At least one sensor measures oxygen levels of the blood in the mixture of deoxygenated and oxygenated blood.

The presently preferred embodiments may enable the operator to provide more accurate oxygenation levels for cardiac circulation and controlled reoxygenation of the human heart during resuscitation. The use of the preferred embodiments may, in particular, improve the protection of the actively ischemic heart or the heart of cyanotic patients.

DETAILED DESCRIPTION OF THE DRAWINGS AND THE PRESENTLY PREFERRED EMBODIMENTS

Figure 1:
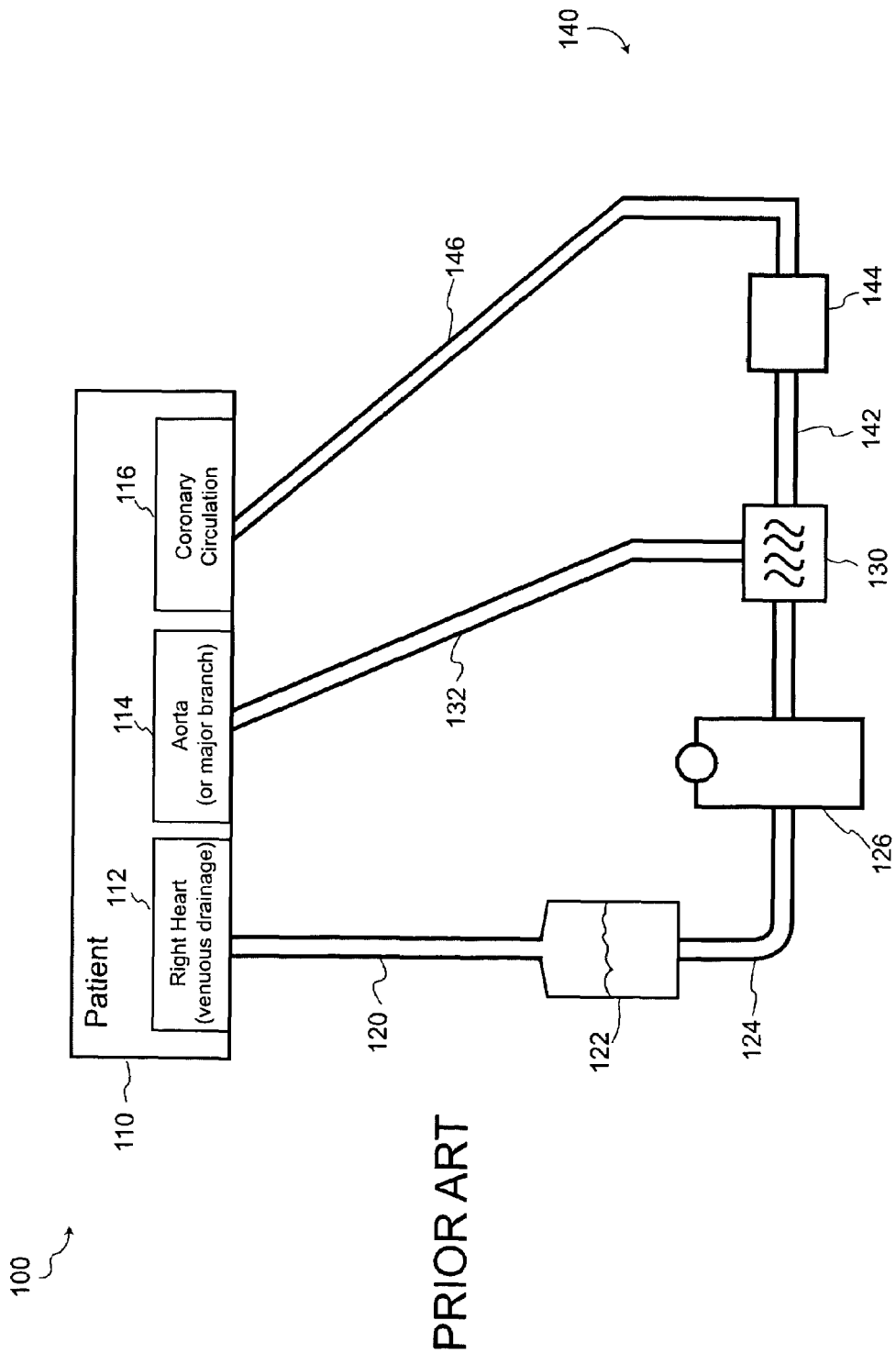
FIG. 1 is a block diagram of a standard cardiopulmonary bypass (CPB) circuit.

FIG. 1 illustrates the prior art of the typical cardiopulmonary bypass circuit 100. The patient 110 has cannulae connected to different structures of the heart (or great vessels) for drainage and appropriate perfusion that are in turn connected to the tubing of the CPB circuit. The CPB circuit receives drainage from the right heart 112, delivers oxygenated blood to the aorta (or other major branch) 114 and delivers cardioplegia for coronary circulation 116. The venous drainage pathway 120 receives blood from right atrium, great veins (i.e., the inferior and superior vena cavae) or both for venous drainage via venous cannula (or cannulae) and a variable length of tubing. The blood received in the venous pathway 120 is then collected in a blood reservoir 122. The reservoir 122 is typically open (or vented) to the atmosphere, but may be closed, and briefly stores the deoxygenated blood. A pump head 126 pumps the deoxygenated blood through the circuit's tubing 124 to a hollow fiber membrane oxygenator 130. The oxygenator 130 may eliminate carbon dioxide and/or other waste products from the blood and provides oxygen by exposure of the membrane to a supply of oxygen typically given as either pure gaseous oxygen or mixed with a supply of room air.

As one skilled in the art would appreciate, the oxygenator 130 may take several different forms. For example, the oxygenator 130 may also be a bubble or membrane oxygenator. Similarly, the pump 126 may comprise a variety of different types of pumps. For example, a roller pump or centrifugal pump, in which the speed of the spinning head (and the resistance of the system) determines the flow of blood or perfusate, may be used.

Upon exiting the oxygenator 130, oxygenated blood is sent through the systemic perfusion pathway 132. The systemic perfusion pathway 132 connects with the aortic cannula (not shown), which in turn connects with the aorta (or other major branch) 114. The systemic perfusion pathway 132 typically includes a length of tubing and a filter that traps small particles and microbubbles (not shown). The flow of the oxygenated blood to the systemic pathway 132 is controlled by the pump 126.

In a typical cardiopulmonary bypass set up, a portion of the oxygenated blood is also sent through the cardioplegia circuit 140, which circulates a blood-crystalloid mixture to the heart itself. The cardioplegia portion 140 of the circuit 100 includes a length of tubing 142 that connects the oxygenator 130 to a cardioplegia delivery system 144. The cardioplegia delivery system 144 mixes the blood and crystalloid to form the cardioplegia. Connected to the cardioplegia delivery system 144 is a cardioplegia delivery pathway 146 that delivers cardioplegia to the coronary circulation 116. The delivery of cardioplegia through the cardioplegia delivery pathway 146 is typically accomplished through an antegrade cardioplegia needle inserted into the aortic root, a retrograde cardioplegia catheter inserted into the coronary sinus, a handheld cardioplegia catheter that can be inserted into the coronary ostium, or a combination thereof.

Cardioplegia systems include systems in which a predetermined and/or consistent blood-crystalloid ratio perfusate is delivered throughout the procedure, but may include more complex systems in which subtle alterations in blood-crystalloid ratios can be effected and in which pharmacologic agents (drugs) can be administered in a very precise manner. To administer cardioplegia to the heart (coronary circulation), blood is generally mixed in a 3:1 or 4:1 ratio with a crystalloid solution, which stops the heart when applied through the cardioplegia delivery pathway 146. In the alternative, a blood and crystalloid mixing system or reservoir 144 is an integrated cardioplegia delivery system. Such systems allow for control over a number of factors involved in cardioplegia delivery. For example, precise ratios of blood to crystalloid can be dialed in and medication adjustments can be precisely controlled allowing for the administration of things like insulin, adenosine or other drugs.

Figure 2:
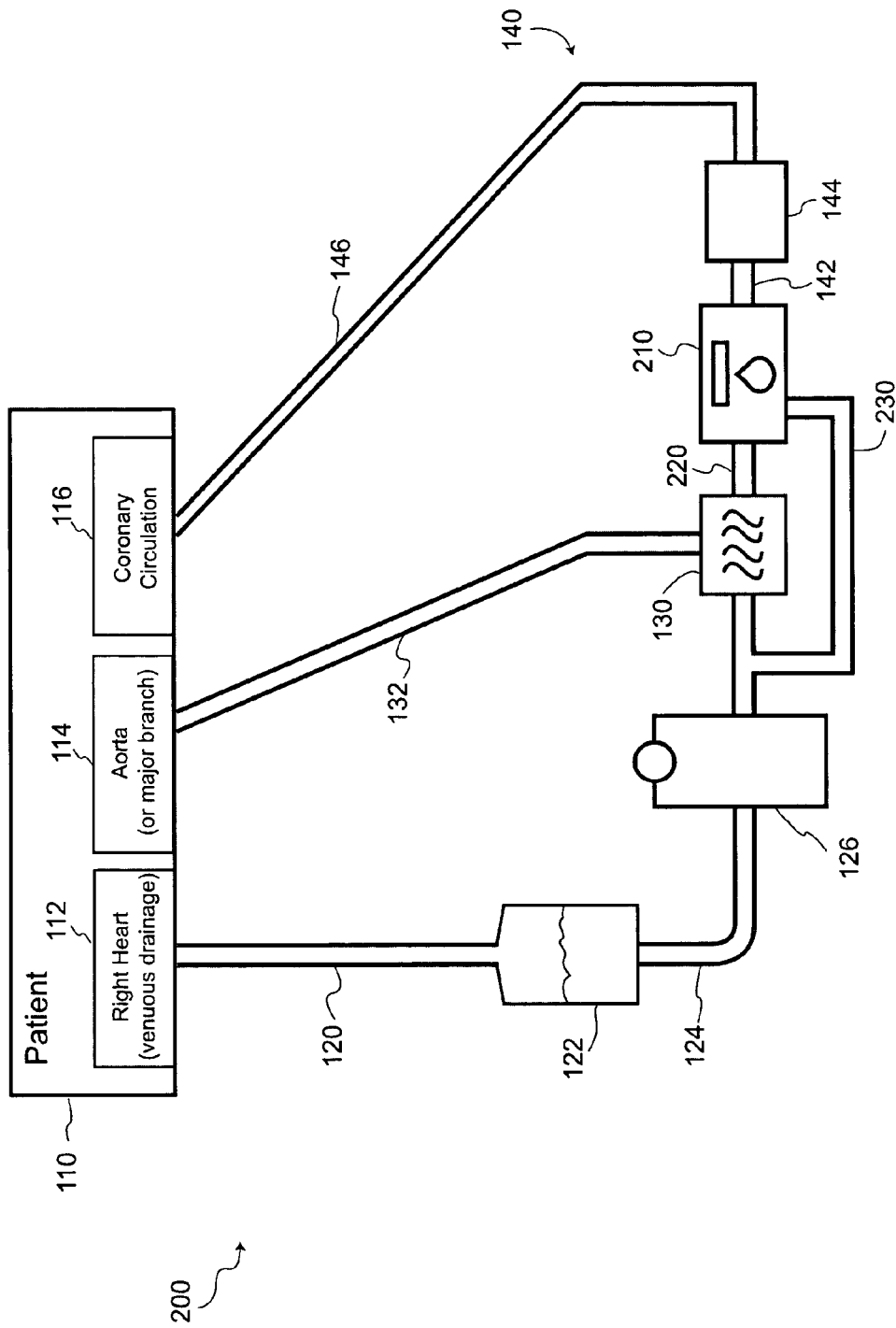
FIG. 2 is a block diagram of a cardiopulmonary bypass (CPB) circuit incorporating one embodiment.

FIG. 2 shows a block diagram of a cardiopulmonary bypass circuit 200 utilizing an embodiment of a cardioplegia circuit. The circuit 200 includes an oxygenation controller 210. The oxygenation controller 210 is a microprocessor, a general processor, a controller, an application specific intergrated circuit, a transistor, a field programmable gate array, an analog circuit, a digital circuit, valves, pumps, filters, tubing, a reservoir or bladder or a series of the same, relays, sensors, pulse oximetry sensors, combinations thereof or other now known or later developed devices for mixing fluids from two different sources by using data relating to partial pressure of oxygen, oxygen saturation, or oxygen content or level in the fluids. The oxygenation controller 210 is connected with tubing 220, which carries oxygenated blood from the oxygenator 130, and tubing 230, which carries deoxygenated blood from the venous reservoir 122. The oxygenation controller 210 allows the perfusionist to adjust the oxygen levels of the blood sent to the cardioplegia pathway 146. In one embodiment, the oxygenation controller 210 includes a dial for adjusting the output oxygenation level and a real-time display for parameters such as oxygen saturation and partial pressure of oxygen ($pO_2$). In other preferred embodiments, the oxygenation controller 210 may include one or more of a variety of different input devices, including buttons, knobs, a mouse, a trackball, sliders, touch pads, sensors or touch screens, to control parameters of the output blood.

The oxygenation controller 210 mixes oxygenated and deoxygenated blood in a ratio, which results in a carefully controlled oxygenation saturation and $pO_2$ level, and delivers this blood to the cardioplegia system 140 by way of the tubing 142. The tubing 142 connects the blood output by the oxygenation controller 210 to the cardioplegia delivery system 144. The cardioplegia delivery system 144 then provides the cardioplegia from the oxygenation controller blood mixture and crystalloid. The cardioplegia is delivered to the coronary circulation 116 via the cardioplegia delivery pathway 146.

Figure 3:
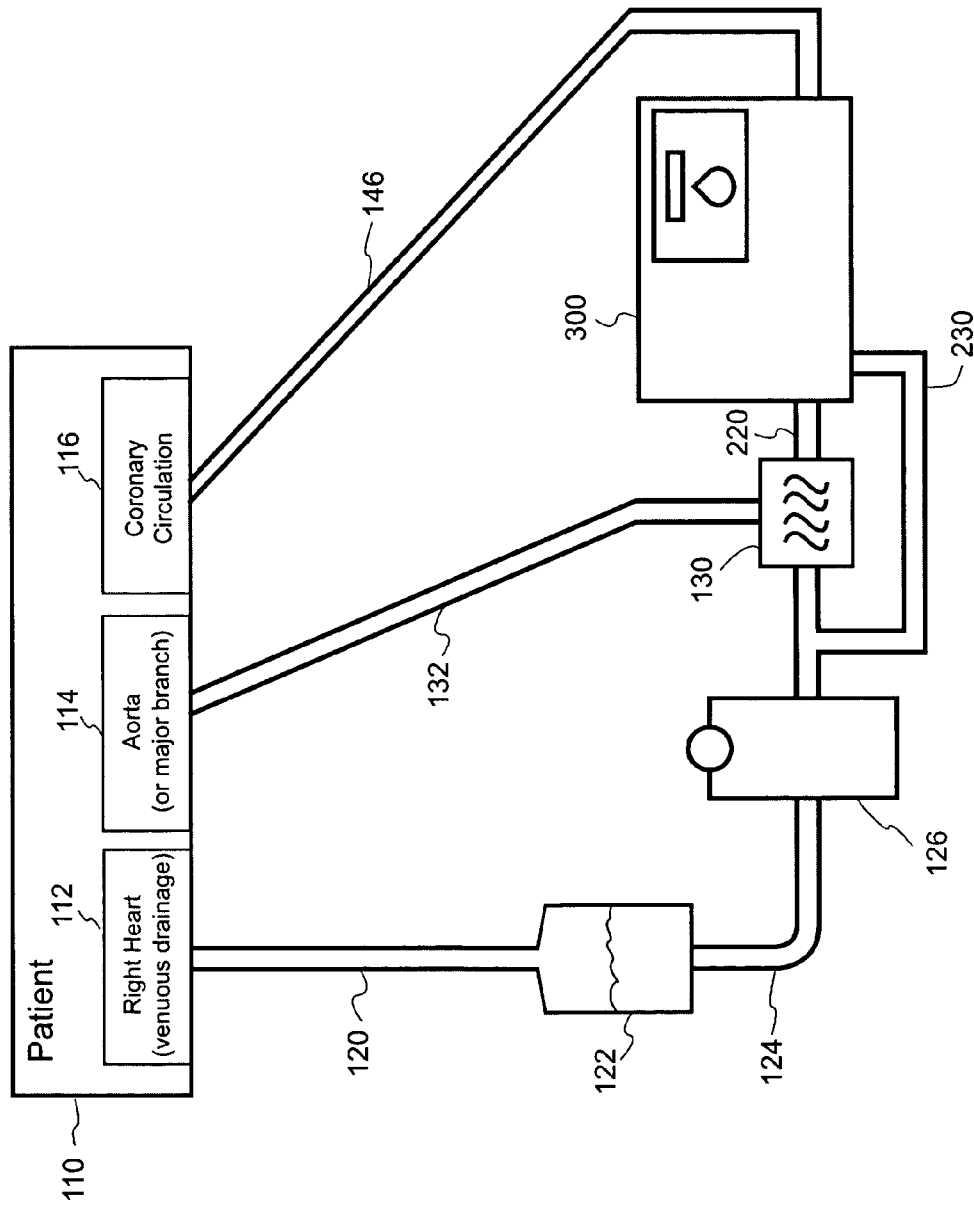
FIG. 3 is a block diagram of a cardiopulmonary bypass (CPB) circuit incorporating another embodiment.

As shown in FIG. 3, the oxygenation controller 210 may also be encompassed in an integrated cardioplegia delivery apparatus 300. The integrated cardioplegia delivery apparatus 300 includes both the oxygenation controller 210 and the cardioplegia delivery system 144.

Figure 4:
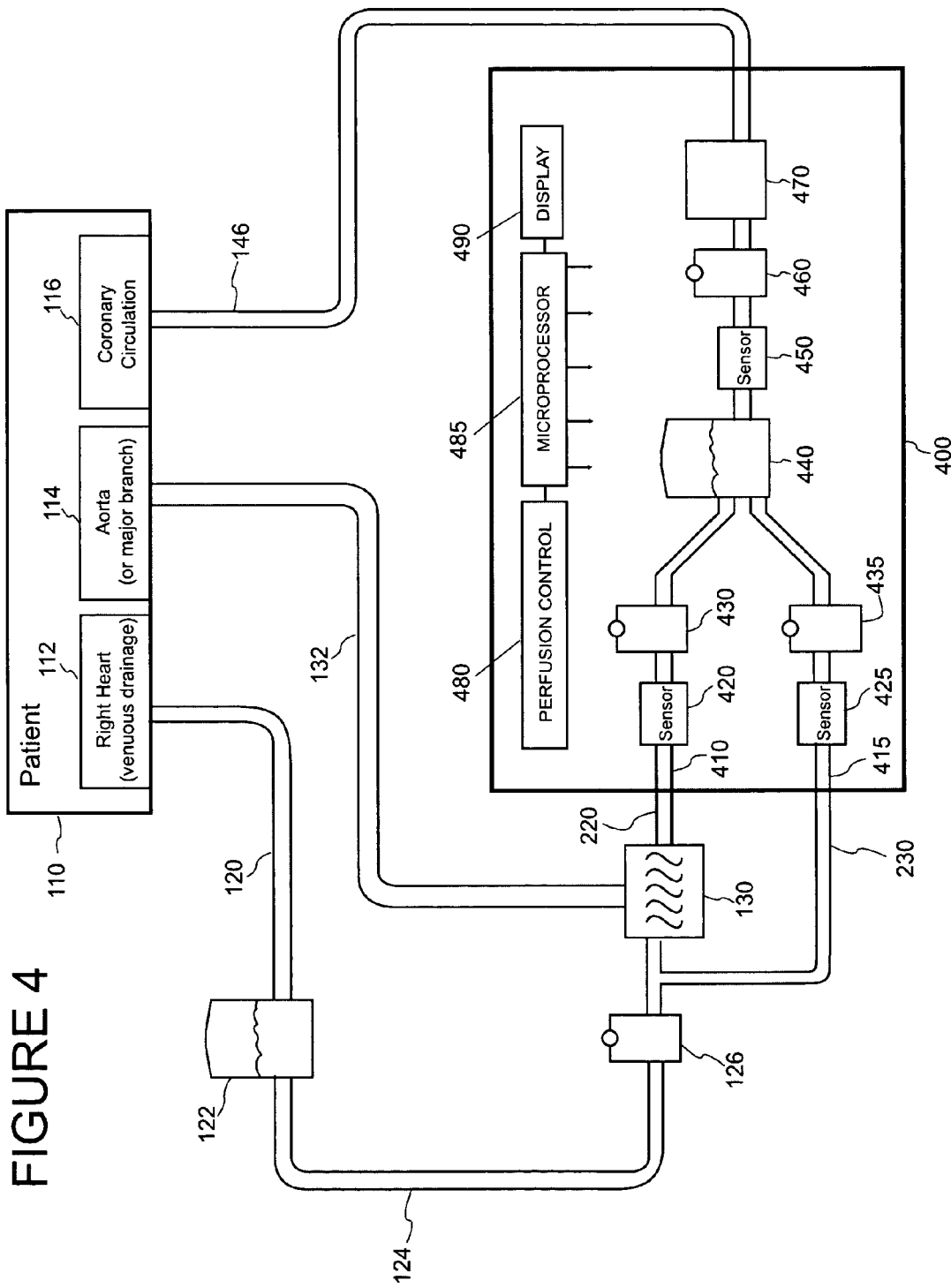
FIG. 4 is a block diagram of another embodiment of a cardiopulmonary bypass circuit.

FIG. 4 depicts another embodiment of an oxygenation controller 400, in which the oxygenation control and cardioplegia delivery are integrated. The oxygenation controller 400 includes two inputs: an oxygenated blood input 410 and deoxygenated (venous) blood input 415. The oxygenated blood input 410 receives oxygenated blood directly or indirectly from the oxygenator 130. The oxygen partial pressure and saturation levels are measured by a sensor 420. Pump 430 controls the flow of oxygenated blood to reservoir 440. As one skilled in the art would appreciate, the pumps may take a variety of forms. For example, a centrifugal pump, roller pump, a piston-based arrangement that may affect flow by the application of pressure onto previously described bladder reservoirs, or any now known or later developed device suitable for controlling the flow of fluids may be used.

The deoxygenated blood input 415 directly or indirectly receives blood that was collected in the venous reservoir 126. The oxygen partial pressure and saturation levels are measured by sensor 425. The sensor 425 is the same or a different type of sensor than used for the sensor 420. Pump 435 controls the flow of deoxygenated blood to reservoir 440. The pump 435 is the same or different type of pump as pump 430.

Reservoir 440 holds the mixture of deoxygenated and oxygenated blood thereby providing a mixed blood supply. As one skilled in the art would appreciate, the mixed blood supply may take the form of being held in a reservoir, or may stream through a blood line, a line of tubing, or any other device that may contain a volume of blood. Sensor 450 is the same or a different type of sensor as sensors 420 and 425. The sensor 450 measures the oxygen partial pressure and saturation levels for the blood in reservoir 440. Pump 460 is the same or different type of pump as pumps 126, 430 or 425. The pump 460 pumps the mixed blood to cardioplegia solution injector 470, which then outputs the resultant perfusate solution for delivery via cannula 146.

Microprocessor 485 receives data from sensors 420, 425 and 450, pumps 430, 435 and 460, and perfusion control input 480. The microprocessor 485 is a general processor, digital signal processor, application specific integrated circuit, a field programmable gate array, a control processor, an analog circuit, a digital circuit, a network, combinations thereof or other now known or later developed device for controlling a mixing ratio. The microprocessor 485 also controls the output of display 490 and the pumps 430, 435 and 460, but separate processors may be used for these functions. If included in the oxygenation controller 400, the cardioplegia solution injector 470 may also be controlled by the microprocessor 485 or a different processor.

Sensors 420 and 425 provide the microprocessor 485 with data about the deoxygenated and reoxygenated blood received at inputs 410 and 420. The microprocessor 485 uses the data received from sensor 420 and 425 to control the rate at which pumps 430 and 435 operate. The sensors may be constructed using fiberoptics for oximetry readings, continuous blood gas analysis, or any other method in which real-time blood chemistry levels, such as $pO_2$ or oxygen saturation, may be obtained.

Sensor 450 provides the microprocessor 485 with data about the blood mix contained in the reservoir 440. In alternative embodiments, the reservoir 440 may be replaced with a Y coupling. In such embodiments, the sensor may be located at the output of the Y couple to provide data to the microprocessor 485. The microprocessor then instructs pump 460 to output the mixed oxygenated and deoxygenated blood.

Perfusion control 480, such as a memory, processor, data bus, user input device or a data port, allows a perfusionist to control the oxygen partial pressure and saturation levels. The perfusion control 480 provides the microprocessor 485 with the desired parameters. Utilizing the data received from the sensors 420, 425 and 450, the microprocessor 485 can control pumps 430, 435 and 460 to insure that the desired oxygenation levels of the outputted blood are achieved.

The display 490 is a monitor, CRT, LCD, projector, LED or other now known or later developed display device. The display 490 provides visual feedback to the perfusionist. The display 490 may provide data on the input and output oxygenation levels, blood flow rates, pressure levels or combinations thereof. Additional data relating to the blood, crystalloid mixture or other aspects related to the cardioplegia solution may also be displayed. In a preferred embodiment, the display 490 and perfusion control 480 are combined in a single touch screen.

In another embodiment, the cardioplegia solution injector 470 may be separate from the oxygenation controller 400. As shown in FIG. 2, the cardioplegia delivery system 144 may operate independently from the oxygenation controller 210.

In other embodiments, the reservoir may be omitted, other reservoirs may be used, and the pumps may be located at a variety of different locations. For example, reservoirs or bladders for deoxygenated, oxygenated and mixed blood may be used. Sensors 420, 425 and 450 may be connected with the deoxygenated, oxygenated and mixed blood reservoirs or bladders, respectively, or a subset thereof. Further, the reservoirs and connected sensors 420, 425, and 450 may all be integrated into a disposable bladder. The flow rate of each of the reservoirs within the disposable bladder (and consequently the mixture level in mixed blood reservoir 440) then may be controlled by pumps 430, 435, and 460, which are in contact with the disposable bladder. The pumping rates of pumps 430, 435, and 460 may be controlled by the microprocessor 485, which receives data from sensors 420, 425 and 450. Alternatively, separate bladders may be used for each reservoir.

Alternatively, in an embodiment in which the reservoirs are omitted, sensors 420, 425, and 450 may be implemented in Y-shaped tubing, in which sensors 420 and 425 are located proximate to the two inputs of the Y-shaped tubing and sensor 450 is proximate to the single output of the Y-shaped tubing. In this embodiment, the microprocessor 485 may receive data from sensors 420, 425, and 450 and control pumps 430 and 435 to provide a desired mixed blood ratio and flow rate of the mixed blood.

Additionally, other sensors may be added to incorporate measurement of other parameters of the deoxygenated blood, the blood received from the oxygenator, the crystalloid mixture, and the overall mixture provided to the cardioplegia delivery pathway. The sensors may be in a variety of locations. For example, sensors may be located in reservoirs, pumps, or tubing. A fewer number of sensors may be used, such as only one sensor at an output of the mix or two sensors at the two inputs without a sensor at the output.

In yet another embodiment, the microprocessor may control a timing mechanism that gauges the time frame in which specific levels of oxygenation (or other parameters) occur. Alarm mechanisms may also be incorporated to send a warning to the perfusionist concerning whether input or output blood levels are low, whether the oxygenation levels are too high or too low, or whether the crystalloid mixture should be adjusted. The alarms can be controlled by the microprocessor 485 based on the sensor or other information received and displayed on the display 490. Additionally, another microprocessor may control the operation of the oxygenation controller 400.

In a further embodiment, the oxygenation system may control all parameters and provide a simple way to dial in oxygen levels to be output to the systemic perfusion pathway 132 and cardioplegia delivery pathway 146. In this regard, real-time adjustments may be made through a single device to provide accurate levels of oxygen provided to brain and heart.

Figure 5:
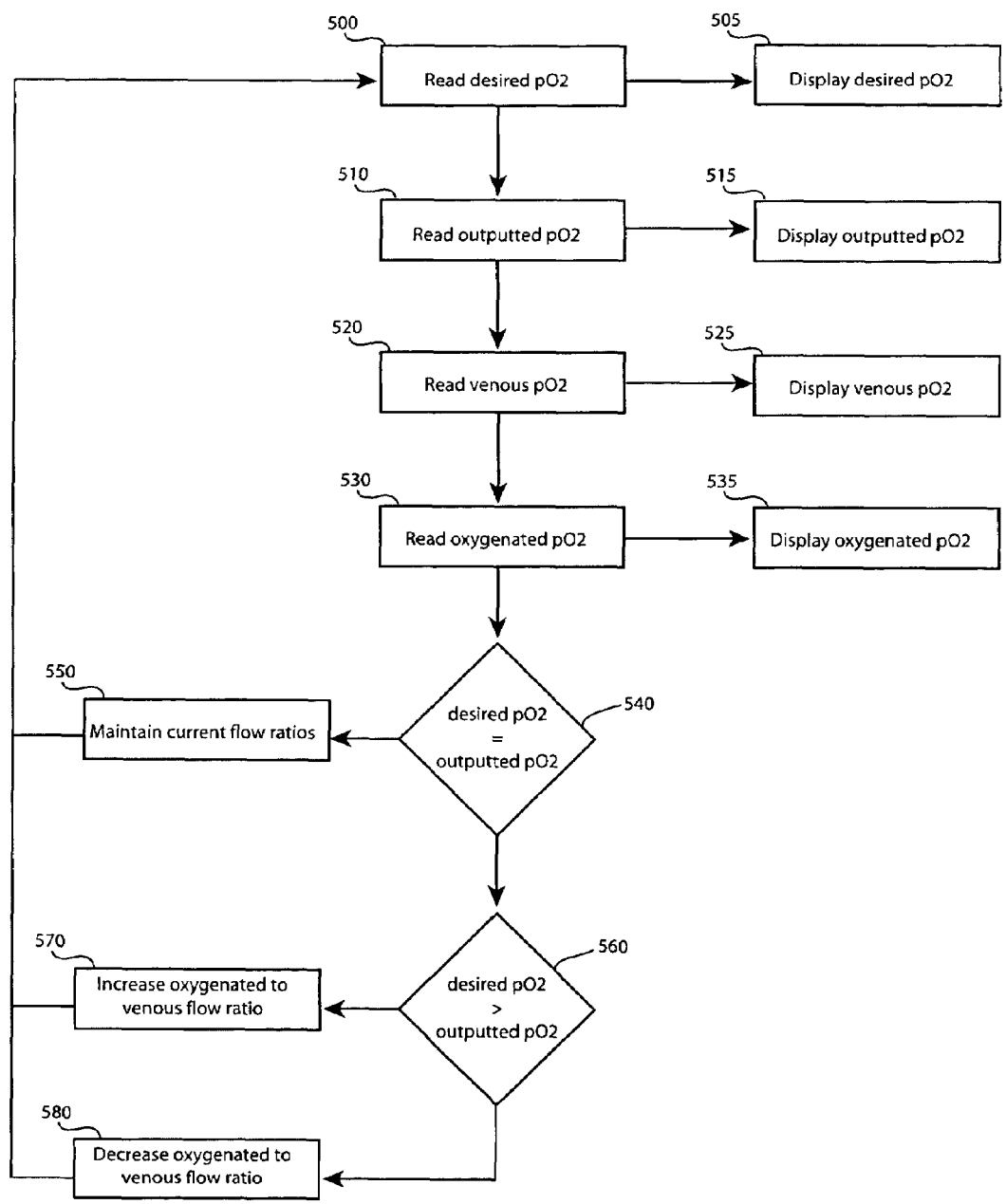
FIG. 5 is a flowchart depicting microprocessor control of oxygenation levels for cardiac circulation in accordance with one embodiment.

FIG. 5 shows a flowchart for microprocessor control in one embodiment. In act 500, the microprocessor reads a desired partial pressure of oxygen level, which is input by a user and has been stored in memory. A variety of memory devices may be used to store data, including memory that is integrated with the microprocessor. In act 505, the desired partial pressure of oxygen level is displayed. In act 510, the microprocessor reads the actual partial pressure of oxygen level from a sensor. This information is displayed in act 515. In acts 520 and 530, the microprocessor reads the partial pressure of oxygen levels of the venous blood and oxygenated blood, from respective sensors. In acts 525 and 535, the respective levels are displayed.

In act 540, the microprocessor compares the desired partial pressure of oxygen level with the output partial pressure of oxygen level to determine if they are substantially equal. The microprocessor can be set with fixed or varying tolerances in assessing this condition. For example, the microprocessor may be set such that a 5 percent difference in levels is considered to satisfy the requirement that the levels are equal. If the equality condition is satisfied, the microprocessor maintains the current oxygenated to venous blood flow ratio in act 550, and returns to act 500. If the equality condition is not satisfied, the microprocessor proceeds to act 560.

In act 560, the microprocessor assesses whether the desired partial pressure of oxygen level is greater or less than the actual outputted partial pressure of oxygen level. If the desired level is greater than the actual level, the microprocessor directs the pump heads to increase the oxygenated to venous blood flow ratio in act 570. If the desired level is smaller than the actual level, the microprocessor directs the pump heads to decrease the oxygenated to venous blood flow ratio in act 580. After act 570 or 580, the microprocessor returns to act 500.

The flowchart depicted in FIG. 5 is one example of how the microprocessor can be programmed to provide actual mixtures of the venous and reoxygenated blood. This process can be performed in a variety of different steps and in a different order. Further, the microprocessor may also be used to evaluate different blood chemistry levels, such as pH, partial pressure of $CO_2$, bicarbonate levels, or oxygen saturation, and provide appropriate mixtures of venous and oxygenated blood to address desired levels of those items. The desired ratio may be altered automatically or manually as a function of time.

It is therefore intended that the foregoing detailed description be regarded as illustrative rather than limiting, and that it be understood that it is the following claims, including all equivalents, that are intended to define the spirit and scope of this invention. For example, while embodiments have been disclosed in the context of a cardiopulmonary bypass circuit, embodiments may also be used in a catheter lab during an angioplasty procedure, during a heart transplant operation, or any other environment in which controlled perfusion and cardiac oxygenation is desired. Accordingly, these embodiments may be used for either during cardiac surgery for unstable coronary syndrome or for long and complex cases involving prolonged surgical times. In such cases, an embodiment may be used as part and parcel of the cardiopulmonary bypass circuit (heart-lung machine). Alternatively, embodiments may also be used as a free-standing mechanism for the control of perfusion and reoxygenation during percutaneous coronary intervention (angioplasty and stent procedures).

Further, the blood oxygen levels measured by the sensors may take a variety of forms. For example, the blood oxygen level may comprise partial pressure of oxygen ($pO_2$) or the percentage of oxygen saturation ($O_2$ saturation). Alternatively, the sensors may measure both partial pressure of oxygen ($pO_2$) and the percentage of oxygen saturation ($O_2$ saturation). In yet another embodiment, the coronary perfusion device addresses blood oxygen levels by considering the total amount of oxygen level in the blood (oxygen content). In this regard, an alternative embodiment may evaluate oxygen content by evaluating $pO_2$, $O_2$ saturation, hemoglobin level, and/or the amount of oxygen dissolved in the blood.

The invention claimed is:

1. A coronary perfusion device, comprising:
    a control input configured to receive a desired blood oxygen level of mixed blood in a mixed blood line;
    a venous blood supply input configured to receive deoxygenated blood from a patient;
    an oxygenated blood supply input configured to receive oxygenated blood from an oxygenator;
    the mixed blood line connected with said venous blood supply input and said oxygenated blood supply input and configured so as to output the mixed blood, the mixed blood comprising a mixture of deoxygenated blood from the venous blood supply input and oxygenated blood from the oxygenated blood supply input;
    a mixed blood sensor configured to measure blood oxygen levels in the mixed blood line; and
    a microprocessor that is programmed to receive data from said control input and said mixed blood sensor;
    wherein the microprocessor is programmed to control the mixing of blood as a function of the desired blood oxygen level; and
    wherein the mixed blood line provides coronary perfusion to the patient.

2. The coronary perfusion device of claim 1 further comprising:
    a venous blood sensor configured to measure oxygen levels of the deoxygenated blood; and
    an oxygenated blood sensor configured to measure oxygen levels of the oxygenated blood;
    wherein the microprocessor is further programmed to receive data from said venous blood sensor and said oxygenated blood sensor.

3. The coronary perfusion device of claim 1 further comprising:
    a venous blood pump connected with the venous blood supply input and configured to adjust flow of venous blood; and
    an oxygenated blood pump connected with the oxygenated blood supply input and configured to adjust flow of oxygenated blood.

4. The coronary perfusion device of claim 1, wherein the oxygen levels are measurements of partial pressure of oxygen in the blood.

5. The coronary perfusion device of claim 1 further comprising a mixed blood supply connected with said mixed blood line, said mixed blood supply configured to hold mixed blood.

6. The coronary perfusion device of claim 1 further comprising a mixed blood supply having a first input connected with said oxygenated blood input, a second input connected with said venous blood input, and output connected with said mixed blood line.

7. The coronary perfusion device of claim 1 further comprising a mixed blood pump connected with said mixed blood line.

8. The coronary perfusion device of claim 1 further comprising a display connected with said microprocessor and configured to display blood oxygen level data.

9. The coronary perfusion device of claim 1 wherein the control input comprises a touch screen.

10. The coronary perfusion device of claim 9 wherein the touch screen is configured to receive a tactile input and display blood oxygen level data.

11. The coronary perfusion device of claim 1 wherein the control input is a dial.

12. The coronary perfusion device of claim 1 wherein the mixed blood sensor measures partial pressure of oxygen in blood.

13. The coronary perfusion device of claim 2 wherein the venous blood sensor and oxygenated blood sensor measure partial pressure of oxygen in blood.

* * * * *